(12) United States Patent
Deng et al.

(10) Patent No.: US 9,626,753 B2
(45) Date of Patent: Apr. 18, 2017

(54) PROGRAMMABLE DIGITAL MACHINE VISION INSPECTION SYSTEM

(71) Applicants: Tyco Electronics (Shanghai) Co. Ltd., Shanghai (CN); Tyco Electronics Corporation, Berwyn, PA (US); Shenzhen AMI Technology Co. Ltd., Guangdong (CN)

(72) Inventors: Yingcong Deng, Shanghai (CN); Dandan Zhang, Shanghai (CN); Roberto Francisco-Yi Lu, Bellevue, WA (US); Lvhai Hu, Shanghai (CN); Zinglong Zeng, Guangdong (CN)

(73) Assignees: Tyco Electronics (Shanghai) Co. Ltd., Shanghai (CN); Tyco Electronics Corporation, Berwyn, PA (US); Shenzhen AMI Technology Co. Ltd., Guangdong (CN)

( * ) Notice: Subject to any disclaimer, the term of this patent is extended or adjusted under 35 U.S.C. 154(b) by 33 days.

(21) Appl. No.: 14/638,652

(22) Filed: Mar. 4, 2015

(65) Prior Publication Data
US 2015/0254833 A1    Sep. 10, 2015

(30) Foreign Application Priority Data
Mar. 5, 2014    (CN) .......................... 2014 1 0079264

(51) Int. Cl.
*G05B 15/00*    (2006.01)
*G05B 19/00*    (2006.01)
(Continued)

(52) U.S. Cl.
CPC .......... *G06T 7/0004* (2013.01); *B07C 5/3422* (2013.01); *B25J 9/1697* (2013.01);
(Continued)

(58) Field of Classification Search
CPC ............ B07C 5/3422; B07C 2501/0063; B25J 9/1697; G01N 21/9515; G01N 21/9081;
(Continued)

(56) References Cited

U.S. PATENT DOCUMENTS 4,556,317 A * 12/1985 Sandland ............ G03F 7/70591
356/237.1
4,876,728 A * 10/1989 Roth ........................ G06K 9/34
348/94

(Continued)

*Primary Examiner* — Nicholas Kiswanto
*Assistant Examiner* — Rachid Bendidi
(74) *Attorney, Agent, or Firm* — Barley Snyder

(57) ABSTRACT

A programmable digital machine vision inspection system is disclosed having a programmable automatic feeding system that supplies elements to be inspected, a programmable robot system, a programmable inspection system, a qualified product receiving container, and an unqualified product receiving container. The programmable robot system has a first vision system with an inspection area, and a robot that grips the supplied element and moves the gripped element to and from the inspection area. The programmable inspection system has a second vision system that identifies features of the elements in the inspection area, and determines whether the element is a qualified product based on the identified features. The qualified product receiving container receives identified qualified products from the robot, and the unqualified product receiving container that receives identified unqualified products from the robot.

18 Claims, 8 Drawing Sheets

(51) Int. Cl.
*G06T 7/00* (2017.01)
*B25J 9/16* (2006.01)
*B07C 5/342* (2006.01)
*G01R 31/28* (2006.01)
*G01N 21/95* (2006.01)

(52) U.S. Cl.
CPC ..... *G01N 21/9515* (2013.01); *G01R 31/2893* (2013.01); *B07C 2501/0063* (2013.01); *G01N 2021/9518* (2013.01); *G01N 2201/1035* (2013.01); *G05B 2219/39106* (2013.01); *G05B 2219/45047* (2013.01); *G05B 2219/45066* (2013.01); *Y10S 901/44* (2013.01); *Y10S 901/47* (2013.01)

(58) Field of Classification Search
CPC ......... G01N 21/909; G01N 2021/9518; G01N 2021/1035; G01R 31/2893; G06T 7/0004; G05B 2219/39106; G05B 2219/45047; G05B 2219/45066
USPC ....... 700/245, 259; 901/14, 44, 47; 356/235, 356/237.2, 237.6; 348/94, 127, 187
See application file for complete search history.

(56) References Cited

U.S. PATENT DOCUMENTS

| | | | | |
|---|---|---|---|---|
| 5,848,705 | A * | 12/1998 | Gianpaolo | G01R 31/2808 198/346.2 |
| 6,024,526 | A * | 2/2000 | Slocum | B25J 17/0216 414/226.01 |
| 2003/0075488 | A1* | 4/2003 | Olson | H01L 21/67271 209/573 |
| 2007/0081714 | A1* | 4/2007 | Wallack | G06K 9/209 382/152 |
| 2008/0014073 | A1* | 1/2008 | Moore | H01L 21/67132 414/796 |
| 2011/0157373 | A1* | 6/2011 | Ye | G06T 7/002 348/187 |
| 2013/0076891 | A1* | 3/2013 | Childress | G01N 21/909 348/127 |

* cited by examiner

PROGRAMMABLE DIGITAL MACHINE VISION INSPECTION SYSTEM

CROSS-REFERENCE TO RELATED APPLICATION

This application claims priority under 35 U.S.C. §119(a)-(d) to Chinese Patent Application No. 201410079264.0, dated Mar. 5, 2014.

FIELD OF THE INVENTION

The invention generally related to a programmable digital machine vision inspection system, and more specifically, related to a programmable digital machine vision inspection system for inspecting complex and tiny electronic components.

BACKGROUND

Conventionally, during the manufacture of electronic components, inspecting complex and tiny elements is generally performed by an operator manually inspecting the elements. Firstly, the operator picks up an electronic component by a clamp and places the electronic component on an inspection table in an inspection area of a vision inspection system. Then, the vision inspection system inspects all surfaces of the electronic component in the inspection area and determines whether the electronic component is a qualified product. If the electronic component is determined as a qualified product, the operator picks up the electronic component by the clamp and places it into a qualified product receiving container. If the electronic component is determined as an unqualified product, the operator picks up the electronic component by the clamp and places it into an unqualified product receiving container. In this way, the conventional inspection and classification of the electronic component is finished.

Conventionally, the production apparatus has a vision inspection function, that is, the production apparatus can achieve the inspection of the elements on line. These production apparatus can automatically feed the elements, automatically inspect the elements and automatically remove the elements from the inspection area. However, these production apparatus in the prior art are limited to inspecting only one or a few types of elements.

In addition, there are individual inspection apparatus for inspecting the elements in an off line manner. However, these individual inspection apparatus are specially used to inspect one kind or one type of element, and cannot inspect different kinds or types of elements. Furthermore, in this vision inspection system, feeding and removing of the elements are performed manually by the operator, decreasing inspection efficiency.

Further, in the vision inspection system, a distance between a camera and the element to be inspected cannot be freely adjusted according to the size of the element to be inspected. Thereby, the accuracy to inspect some extremely small electronic components is limited.

SUMMARY

A programmable digital machine vision inspection system has a programmable automatic feeding system that supplies elements to be inspected, a programmable robot system, a programmable inspection system, a qualified product receiving container, and an unqualified product receiving container. The programmable robot system has a first vision system with an inspection area, and a robot that grips the supplied element and moves the gripped element to and from the inspection area. The programmable inspection system has a second vision system that identifies features of the elements in the inspection area, and determines whether the element is a qualified product based on the identified features. The qualified product receiving container receives identified qualified products from the robot, and the unqualified product receiving container that receives identified unqualified products from the robot.

BRIEF DESCRIPTION OF THE DRAWINGS

The invention will now be described by way of examples, with reference to the accompanying Figures, of which.

DETAILED DESCRIPTION OF THE PREFERRED EMBODIMENTS

Figure 1:
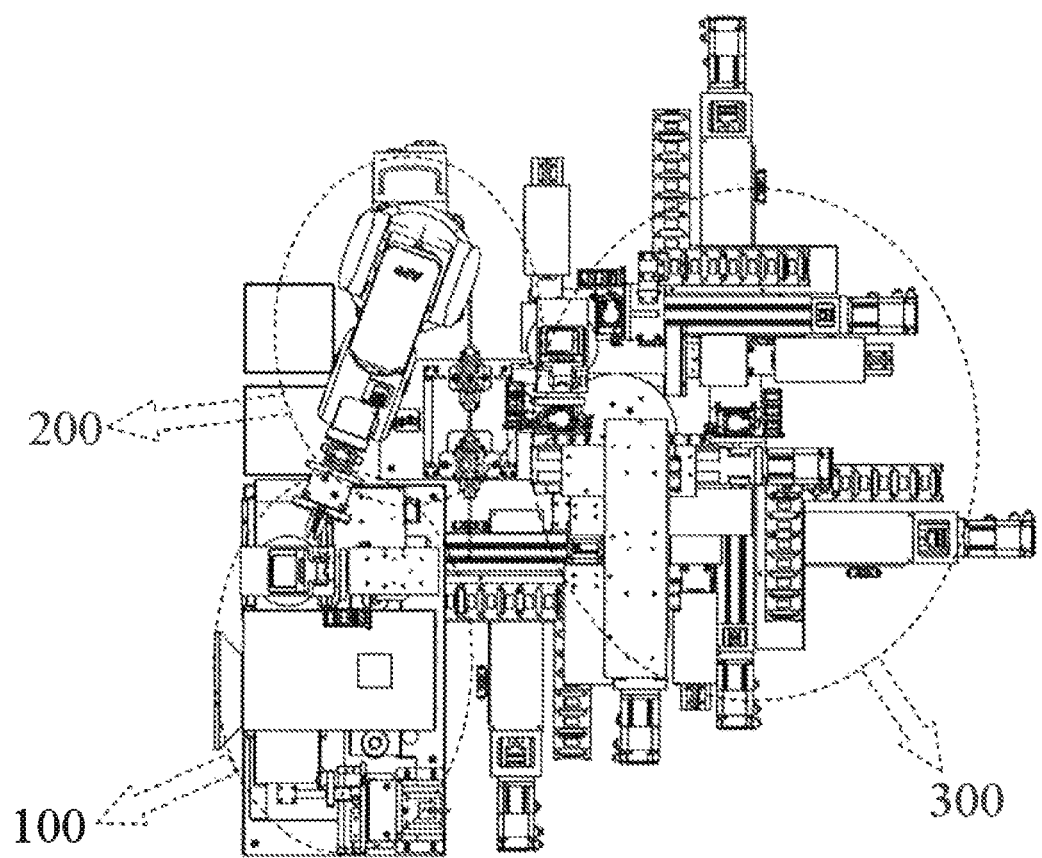
FIG. 1 is a perspective view of function modules of a programmable digital machine vision inspection system.

Exemplary embodiments will be described hereinafter in detail with reference to the attached drawings, wherein like reference numerals refer to like elements. The present disclosure may, however, be embodied in many different forms and should not be construed as being limited to the embodiment set forth herein. Rather, these embodiments are provided so that the present disclosure will be thorough and complete, and will fully convey the concept of the disclosure to those skilled in the art.

In the following detailed description, for purposes of explanation, numerous specific embodiments are described in order to provide a thorough understanding of the disclosed embodiments. One of ordinary skill in the art would appreciate that one or more embodiments may be practiced without these specific details. Well-known structures and devices are schematically shown in order to simplify the drawing.

In an embodiment of FIG. 1, a programmable digital machine vision inspection system has three function modules, the first one of which is a programmable automatic feeding system 100, the second one of which is a programmable robot system 200, and the third one of which is a programmable inspection system 300.

Figure 2:
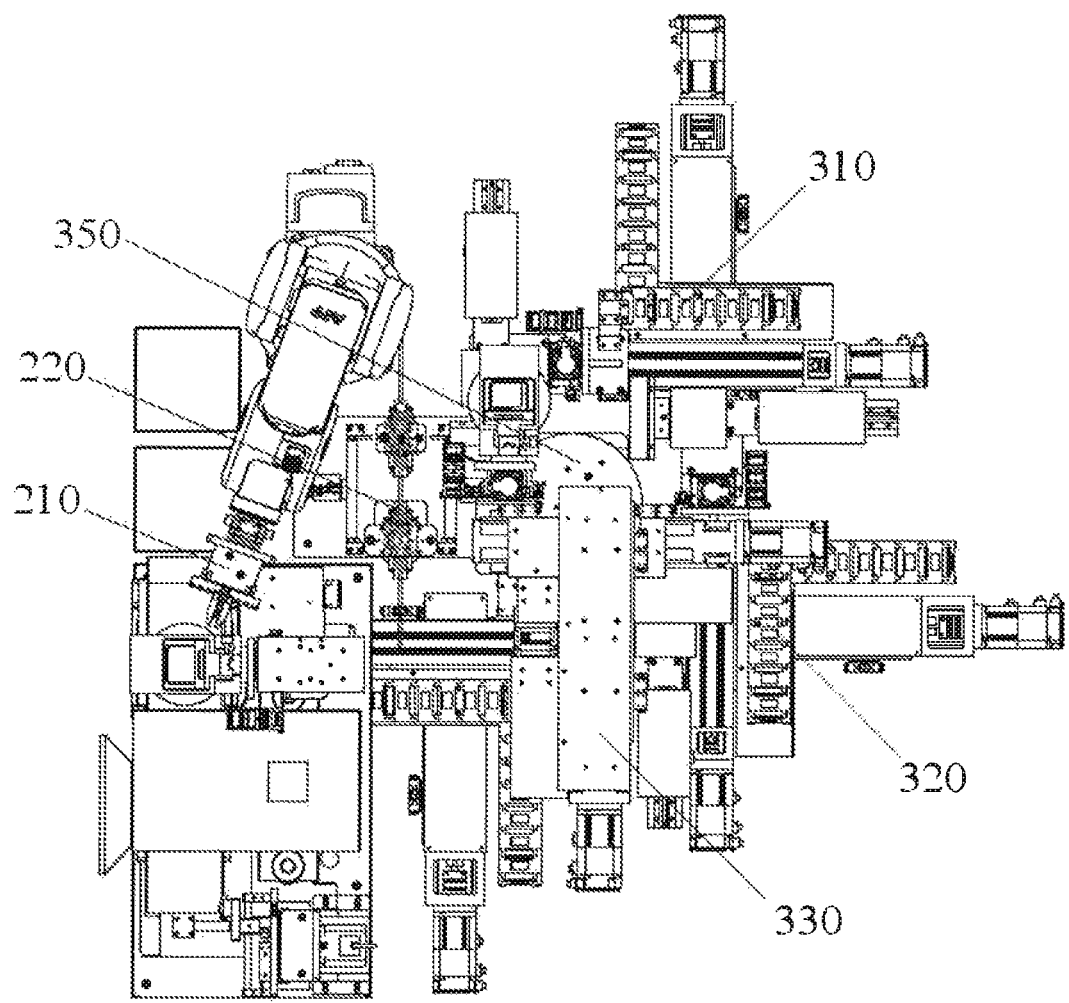
FIG. 2 is a top perspective view of the programmable digital machine vision inspection system.

As shown in the embodiments of FIGS. 1 and 2, the programmable automatic feeding system 100 supplies elements (not shown) to be inspected. The programmable robot system 200 has a robot 210 and a first vision system (described below). The robot 210 grips the element supplied by the programmable automatic feeding system 100 and moves the gripped element into an inspection area, such as an area on a rotatable platform 350 shown in FIG. 2, under the guidance of the first vision system. The programmable inspection system 300 may also have a second vision system (described below). The second vision system identifies features of the elements in the inspection area, and determines whether the element is a qualified product based on the identified features. If the element is determined to be a qualified product, the robot 210 places the element into a qualified product receiving container (not shown). If the element is determined to be an unqualified product, the robot 210 places the element into an unqualified product receiving container (not shown) for receiving the unqualified product.

In this way, an entire inspection process, including feeding elements, picking up elements, inspecting elements, and unloading elements, is automatically controlled and performed by program independent of any manual operation, improving the inspection efficiency.

Figure 3:
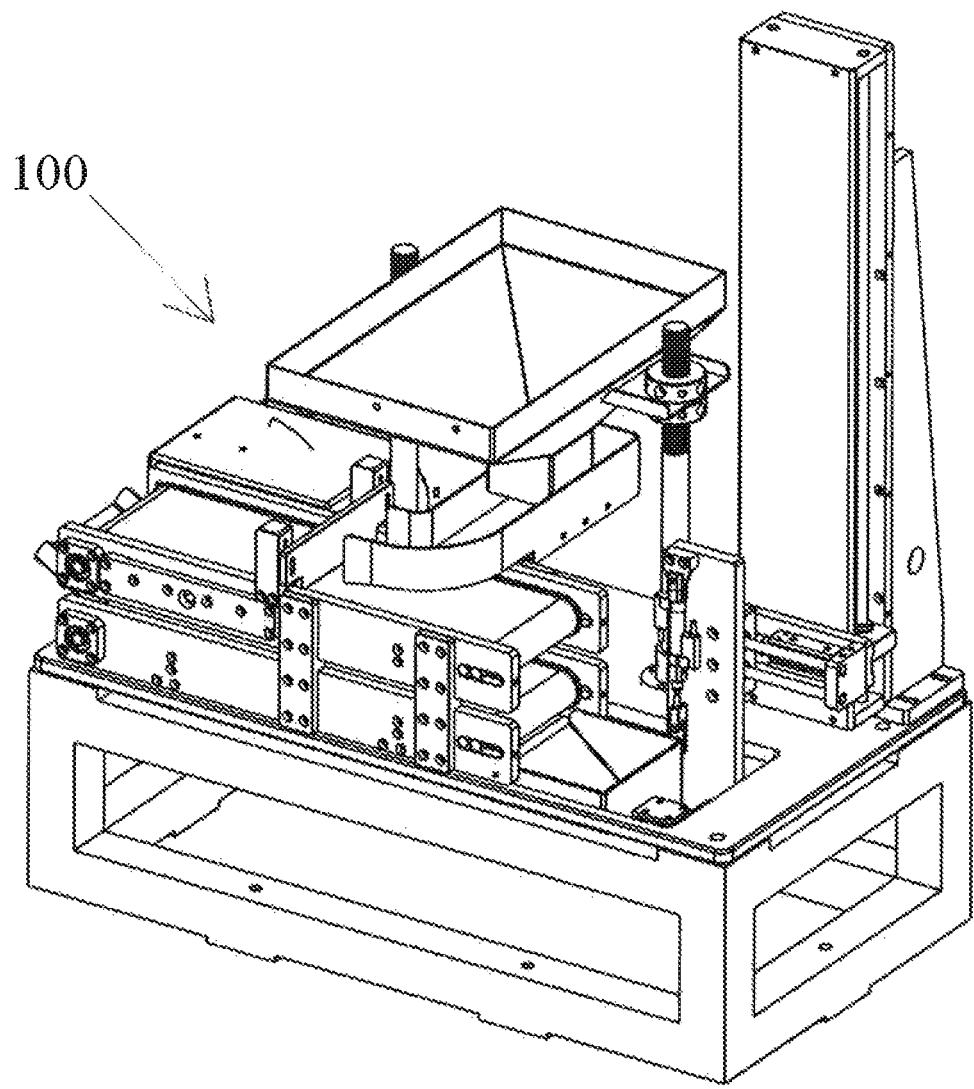
FIG. 3 is a perspective view of a programmable automatic feeding system.

In an embodiment of FIG. 3, the programmable automatic feeding system 100 may be any suitable, known programmable automatic feeding system. The known programmable automatic feeding system may be, for example, the programmable automatic feeding system disclosed in a Chinese patent application No. 201310495091.6, filed on Oct. 21, 2013, the whole disclosure of which is incorporated herein by reference.

In an embodiment of FIG. 2, the programmable robot system 200 has a tool cabinet 220. The robot 210 selects a suitable tool from the tool cabinet 220 and automatically replaces a current tool with the selected tool thereon, all under the guidance of the first vision system. In this way, the robot 210 may grip different kinds or types of elements by selecting the appropriate tool from an array of available tools.

Figure 4:
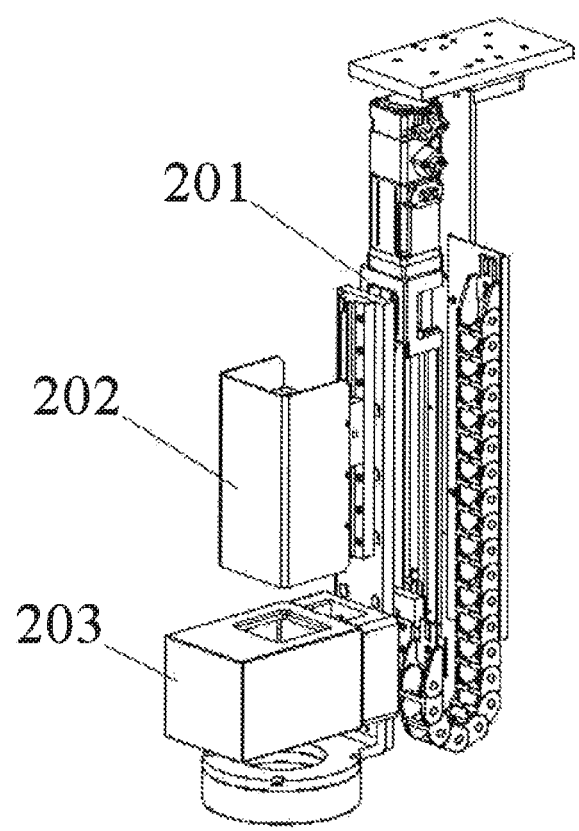
FIG. 4 is a perspective view of a first vision system.

In an embodiment of FIG. 4, the first vision system may be positioned above the programmable automatic feeding system 100 shown in FIG. 3. In an embodiment, the first vision system has a first camera 202 movable in at least one direction, so as to adjust a distance between the first camera 202 and the element to be inspected, and to adjust a distance between the first camera 202 and the robot 210.

Figure 5:
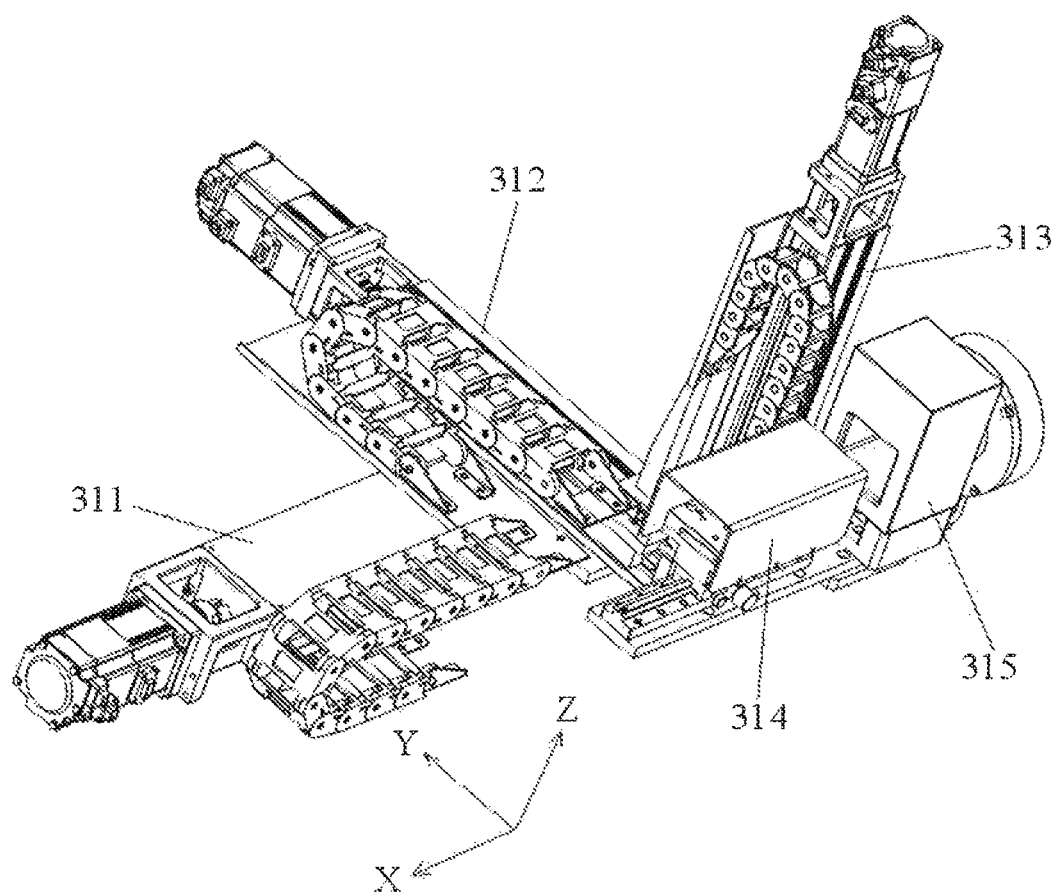
FIG. 5 is a perspective view of a first sub inspection system of a second vision system.
Figure 6:
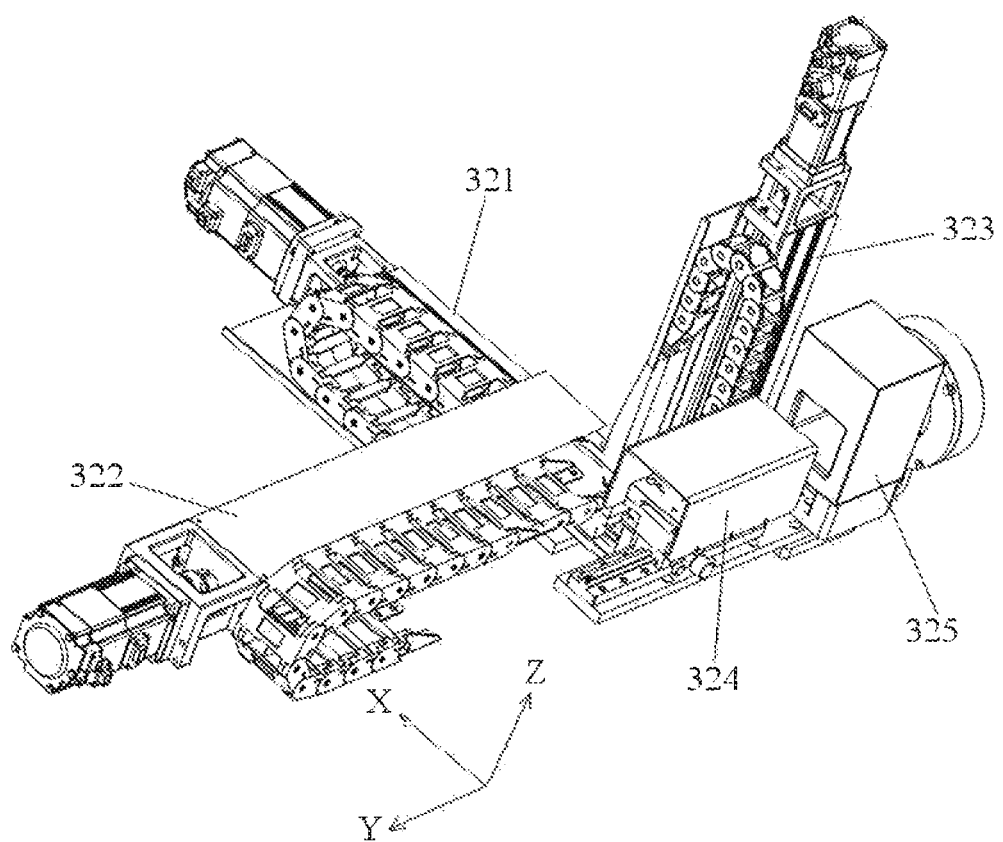
FIG. 6 is a perspective view of a second sub inspection system of the second vision system.

In the embodiment of FIG. 4, the first camera 202 is mounted on a movable arm 201 to move together with the movable arm 201 in a vertical direction Z (see FIGS. 5-6). However, the invention is not limited to the illustrated embodiment. In other embodiments, the first camera 202 may be capable of moving in at least one of a first horizontal direction X (see FIGS. 5-6), a second horizontal direction Y (see FIGS. 5-6) and/or the vertical direction Z as a second camera shown in FIGS. 5-7. In another embodiment, the first camera 202 may be capable of moving in any direction different from the first horizontal direction X, the second horizontal direction Y and the vertical direction Z.

In an embodiment of FIG. 4, the first vision system has a first light source 203 mounted on the movable arm 201 and movable together with the first camera 202. The first light source 203 provides illumination for the first camera 202. In an embodiment, the first light source 203 is capable of automatically controlling and adjusting an intensity, color and other property parameters of a light emitted therefrom, through a program.

In an embodiment of FIG. 5, the programmable inspection system 300 includes a first sub inspection system 310. The first sub-inspection system 310 has a first movable arm 311 movable in the first direction X; a second movable arm 312 mounted on the first movable arm 311 and movable in the second direction Y; a third movable arm 313 mounted on the second movable arm 312 and movable in the third direction Z; and a second camera 314 mounted on the third movable arm 313. In this way, the second camera 314 is capable of moving in at least one of the first direction X, the second direction Y and/or the third direction Z, so as to adjust a distance between the second camera 314 and the element to be inspected.

In the embodiment of FIG. 5, the first direction X is a first horizontal direction; the second direction Y is a second horizontal direction perpendicular to the first horizontal direction; and the third direction Z is a vertical direction perpendicular to the first horizontal direction and the second horizontal direction.

As shown in FIG. 5, the first sub inspection system 310 further comprises a second light source 315, corresponding to the second camera 314, mounted on the third movable arm 313 to move together with the corresponding second camera 314. The second light source 315 provides illumination for the second camera 314. In an embodiment, the second light source 315 automatically controls and adjusts an intensity, color and other property parameters of a light emitted therefrom, through a program.

As shown in FIG. 5, the second camera 314 has an optical axis extending in the first horizontal direction X, so as to capture an image of the element in the first horizontal direction X.

FIG. 6 is an illustrative perspective view of a second sub inspection system 320 of the second vision system of the programmable inspection system in the programmable digital machine vision inspection system of FIG. 1.

As shown in FIG. 6, the programmable inspection system 300 includes the second vision system, which has a second sub-inspection system 320. The second sub-inspection system 320 has a first movable arm 321 movable in the first direction X; a second movable arm 322 mounted on the first movable arm 321 and movable in the second direction Y; a third movable arm 323 mounted on the second movable arm 312 and movable in the third direction Z; and a second camera 324 mounted on the third movable arm 323. In this way, the second camera 324 is capable of moving in at least one of the first direction X, the second direction Y and the third direction Z, so as to adjust a distance between the second camera 324 and the element to be inspected.

In an embodiment of FIG. 6, the second sub inspection system 320 includes a second light source 325, corresponding to the second camera 324, and mounted on the third movable arm 323 to move together with the corresponding second camera 324. The second light source 325 provides illumination for the second camera 324. In an embodiment, the second light source 325 automatically controls and adjusts an intensity, color and other property parameters of a light emitted therefrom, through a program.

In an embodiment, the second camera 324 has an optical axis extending in the second horizontal direction Y, so as to capture an image of the element in the second horizontal direction Y.

Figure 7:
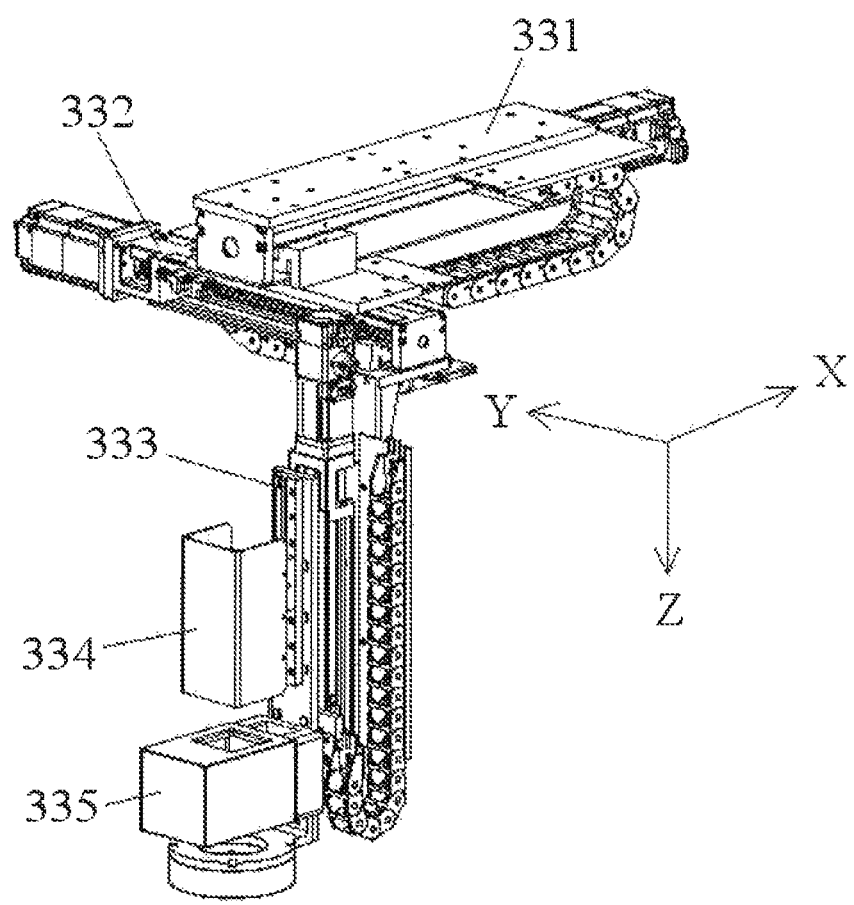
FIG. 7 is a perspective view of a third sub inspection system of the second vision system.

FIG. 7 is an illustrative perspective view of a third sub inspection system 330 of the second vision system of the programmable inspection system in the programmable digital machine vision inspection system of FIG. 1.

In an embodiment of FIG. 7, the second vision system has a third sub-inspection system 330. The third sub-inspection system 330 has a first movable arm 331 movable in the first direction X; a second movable arm 332 mounted on the first movable arm 331 and movable in the second direction Y; a third movable arm 333 mounted on the second movable arm 332 and movable in the third direction Z; and a second camera 334 mounted on the third movable arm 333. In this way, the second camera 334 is capable of moving in at least one of the first direction X, the second direction Y and the third direction Z, so as to adjust a distance between the second camera 334 and the element to be inspected.

In an embodiment, the third sub inspection system 330 has a second light source 335, corresponding to the second camera 334, mounted on the third movable arm 333 to move with the corresponding second camera 334. The second light source 335 provides illumination for the second camera 334. In an embodiment, the second light source 335 is capable of automatically controlling and adjusting an intensity, color and other property parameters of a light emitted therefrom, through a program.

The second camera 334 has an optical axis extending in the vertical direction Z, so as to capture an image of the element in the vertical direction Z.

In this way, the vision inspection system 300 can inspect different surfaces of the element in different directions.

In an embodiment (not shown), the vision inspection system 300 optionally may include a fourth sub inspection system having a second camera with an optical axis extending in a fourth direction different from any one of the first direction X, the second direction Y and the third direction Z. Except for this parameter, the fourth sub inspection system may be substantially the same as the first, second and third sub inspection systems.

Further, one of ordinary skill in the art would appreciate that in other embodiments, the vision inspection system 300 may include one, two, five or more sub-inspection systems.

Figure 8:
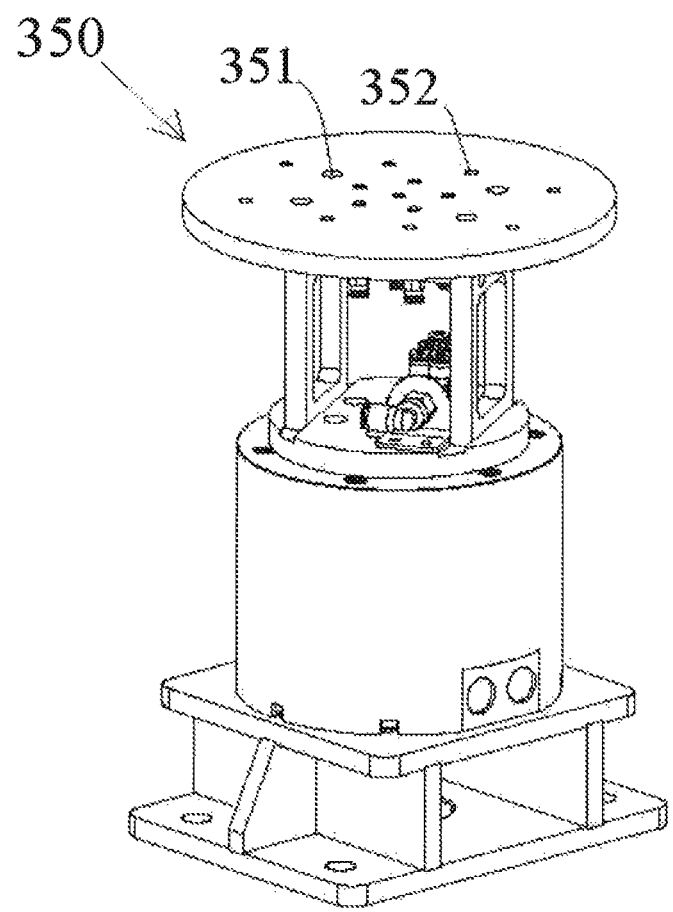
FIG. 8 is a perspective view of a rotatable platform.

In the embodiments of FIGS. 2 and 8, the programmable inspection system 300 has a rotatable platform 350 mounted in the inspection area. The element gripped by the robot 210 is placed on the rotatable platform 350. The rotatable platform 350 is rotatable about the vertical direction Z to change an orientation of the element placed thereon.

In an embodiment, the rotatable platform 350 has a plurality of vacuum suction nozzles 351, 352 configured to suck and position the elements placed on the rotatable platform 350. The plurality of vacuum suction nozzles 351, 352 may have different sizes and shapes, so as to suck and position elements with different sizes and shapes.

One of ordinary skill in this art would appreciate that the above embodiments are intended to be illustrative, and not restrictive. For example, many modifications may be made to the above embodiments by those of ordinary skill in this art, and various features described in different embodiments may be freely combined with each other without conflicting in configuration or principle.

Although several embodiments have been shown and described, it would be appreciated by those of ordinary skill in the art that various changes or modifications may be made in these embodiments without departing from the principles and spirit of the disclosure, the scope of which is defined in the claims and their equivalents.

As used herein, an element recited in the singular and proceeded with the word "a" or "an" should be understood as not excluding a plurality of said elements or steps, unless such exclusion is explicitly stated. Furthermore, references to "an embodiment" of the present invention are not intended to be interpreted as excluding the existence of additional embodiments that also incorporate the recited features. Moreover, unless explicitly stated to the contrary, embodiments "including," "comprising," or "having" an element or a plurality of elements having a particular property may include additional such elements not having that property.

What is claimed is:

1. A programmable digital machine vision inspection system, comprising:
    a programmable automatic feeding system supplying elements to be inspected;
    a programmable robot system having
        a robot that grips the supplied element and moves the supplied element to and from an inspection area, and
        a first vision system having the inspection area and a first camera movable in at least one direction so as to adjust a distance between the first camera and the element to be inspected and a distance between the first camera and the robot;
    a programmable inspection system having a second vision system that identifies features of the elements in the inspection area, and determines whether the element is a qualified product based on the identified features;
    a qualified product receiving container that receives identified qualified products from the robot; and
    an unqualified product receiving container that receives identified unqualified products from the robot.

2. The programmable digital machine vision inspection system according to claim 1, wherein the programmable robot system further comprises a tool cabinet having one or more tools from which the robot selects a suitable tool and automatically replaces a current tool with the suitable tool.

3. The programmable digital machine vision inspection system according to claim 1, wherein the programmable robot system further comprises a movable arm movable in a vertical direction, and onto which the first camera is mounted.

4. The programmable digital machine vision inspection system according to claim 3, wherein the first vision system further comprises a first light source mounted on the movable arm and movable together with the first camera.

5. The programmable digital machine vision inspection system according to claim 4, wherein the first light source automatically controls and adjusts an intensity and a color of the light emitted therefrom by a program control.

6. The programmable digital machine vision inspection system according to claim 1, wherein the second vision system has at least one second camera, each of which is movable in at least one direction to adjust the distance between the second camera and the element to be inspected.

7. The programmable digital machine vision inspection system according to claim 6, wherein the second vision system has a plurality of second cameras that simultaneously identify features of different surfaces of the element positioned in the inspection area.

8. The programmable digital machine vision inspection system according to claim 7, wherein the plurality of second cameras include
    a first directional camera having an optical axis extending in a first direction;
    a second directional camera having an optical axis extending in a second direction perpendicular to the first direction; and
    a third directional camera having an optical axis extending in a third direction perpendicular to the first direction and the second direction.

9. The programmable digital machine vision inspection system according to claim 8, wherein the plurality of second cameras further includes a fourth directional camera having an optical axis extending in a fourth direction different from any one of the first direction, the second direction and the third direction.

10. The programmable digital machine vision inspection system according to claim 9, wherein each of the second cameras is mounted on an individual moving mechanism movable in the first direction, the second direction, or the third direction, such that the second cameras are movable in the first direction, the second direction, and the third direction.

11. The programmable digital machine vision inspection system according to claim 10, wherein the individual moving mechanisms include:
a first movable arm movable in the first direction;
a second movable arm mounted on the first movable arm and movable in the second direction; and
a third movable arm mounted on the second movable arm and movable in the third direction.

12. The programmable digital machine vision inspection system according to claim 11, wherein the second camera is mounted on the first movable arm or the third movable arm of the individual moving mechanism.

13. The programmable digital machine vision inspection system according to claim 12, wherein the first direction is a first horizontal direction; the second direction is a second horizontal direction perpendicular to the first horizontal direction; and the third direction is a vertical direction perpendicular to the first horizontal direction and the second horizontal direction.

14. The programmable digital machine vision inspection system according to claim 13, wherein the second vision system has a plurality of second light sources corresponding to the plurality of second cameras, respectively, and one of each of the second light sources is mounted on the respective moving mechanism of each second camera to move together with the respective second camera.

15. The programmable digital machine vision inspection system according to claim 14, wherein each of the second light sources automatically controls and adjusts an intensity and a color of a light emitted therefrom by a program control.

16. The programmable digital machine vision inspection system according to claim 15, wherein the programmable inspection system has a rotatable platform on which the element gripped by the robot is placed.

17. The programmable digital machine vision inspection system according to claim 16, wherein the rotatable platform is rotatable about the vertical direction to change an orientation of the element placed thereon.

18. The programmable digital machine vision inspection system according to claim 16, wherein the rotatable platform has a plurality of vacuum suction nozzles that suck and secure the elements on the rotatable platform.

* * * * *